United States Patent [19]

Orleck et al.

[11] Patent Number: 5,324,724
[45] Date of Patent: Jun. 28, 1994

[54] COMPOUNDS FOR THE TREATMENT OF SENILE DEMENTIA

[75] Inventors: Barry S. Orlek; Richard E. Faulkner, both of Harlow, England

[73] Assignee: Beecham Group p.l.c., United Kingdom

[21] Appl. No.: 927,678

[22] PCT Filed: Mar. 7, 1991

[86] PCT No.: PCT/GB91/00367
§ 371 Date: Sep. 1, 1992
§ 102(e) Date: Sep. 1, 1992

[87] PCT Pub. No.: WO91/13885
PCT Pub. Date: Sep. 19, 1991

[30] Foreign Application Priority Data

Mar. 14, 1990 [GB] United Kingdom ............... 9005737

[51] Int. Cl.$^5$ .................. C07D 403/04; A61K 31/53
[52] U.S. Cl. ................. 514/214; 514/242; 544/182; 540/585
[58] Field of Search .......... 544/182; 540/585; 514/214, 242

[56] References Cited

FOREIGN PATENT DOCUMENTS 0327155 8/1989 European Pat. Off. .

Primary Examiner—John M. Ford
Attorney, Agent, or Firm—Linda E. Hall; Stuart R. Suter; Edward T. Lentz

[57] ABSTRACT

Azabicyclic compounds, processes for their preparation and their use in the treatment and/or prophylaxis of dementia in animals.

9 Claims, No Drawings

COMPOUNDS FOR THE TREATMENT OF SENILE DEMENTIA

This invention relates to compounds having pharmaceutical activity, to a process for their preparation and their use as pharmaceuticals.

EP-0327155 discloses certain substituted pyrazines, pyrimidines and pyridazines useful in the treatment of senile dementia.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

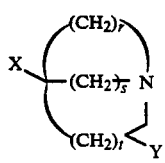
(I)

in which one of X and Y represents hydrogen and the other represents Z, where Z is a group

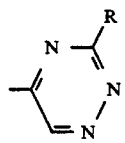

where R is selected from hydrogen, $OR_1$, $SR_1$, $N(R_1)_2$, $NHCOR_1$, $NHCOOCH_3$, $NHCOOC_2H_5$, $NHOR_1$, $NHNH_2$, $C_{2-4}$ alkenyl, $C_{2-4}$ alkynyl, cyclopropyl or $C_{1-2}$ alkyl optionally substituted with $OR_1$, $N(R_1)_2$, $SR_1$, $CO_2R_1$, $CON(R_1)_2$ or one, two or three halogen atoms, in which each $R_1$ is independently hydrogen or $C_{1-2}$ alkyl; r represents an integer of 2 or 3, s represents an integer of 1 or 2 and t represents 0 or 1, with the proviso that when Y is hydrogen s is 1.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

In compounds of formula (I) having two assymmetric centres where Y is other than hydrogen, the stereochemical configuration in which the group Y and the $(CH_2)s$ bridge are on the same side of the plane of the molecule which contains both bridgehead atoms and the ring carbon atom bonded to the group Y will herein be referred to as the exo configuration. Similarly, the configuration of compounds in which the group Y and the bridge $(CH_2)s$ are on opposite sides of the above-mentioned plane of the molecule will herein be referred to as the endo configuration. Preferably compounds of formula (I) have the exo configuration. The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (r, s, t) include (2, 2, 0), (3, 1, 0), (2, 1, 0), (2, 1, 1) and (3, 1, 1).

Preferably $R_1$ is hydrogen or methyl. Preferably R when $C_{1-2}$ alkyl is unsubstituted. Preferred values for R include hydrogen, $C_{1-2}$ alkyl, cyclopropyl, $OR_1$, $SR_1$ or $N(R_1)_2$.

Examples of R include hydrogen, methyl, ethyl, methoxy, methylthio, cyclopropyl, amino and dimethylamino.

R is preferably methyl or ethyl.

The invention also provides a process for the preparation of a compound of formula (I), or a pharmaceutically acceptable salt thereof, which process comprises:

(a) cyclising a compound of formula (II):

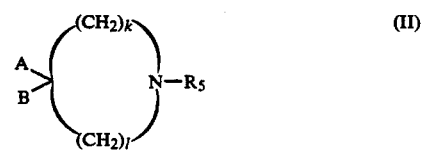
(II)

in which (i) A represents Z or a group convertible thereto and B represents $-(CH_2)_jL_1$ where $L_1$ is a leaving group or A and $L_1$ together represent $-COO-$; one of j, k and l is 1 and the other two independently represent an integer of 2 or 3, and $R_5$ represents hydrogen or an N-protecting group; to give a compound of formula (IIa):

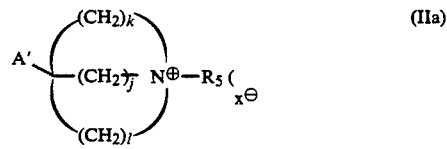
(IIa)

in which A' represents Z or a group convertible thereto, x- is an anion and the remaining variables are as previously defined;

or (ii) A represents an electron withdrawing group, B represents hydrogen and $R_5$ represents $-(CH_2)_j L_2$ where $L_2$ is a leaving group; one of k and l is 1 and the other and j independently represent an integer of 2 or 3; to give a compound of formula (IIb):

(IIb)

in which K represents an electron withdrawing group or A' and the remaining variables are as previously defined; and thereafter, optionally or as necessary and in any appropriate order, removing any $R_5$ N-protecting group, converting K to A', converting A' to Z, optionally interconverting Z and/or forming a pharmaceutically acceptable salt; or (b) cyclising a compound of formula (III):

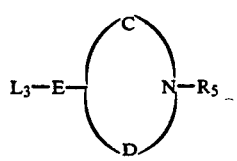

(III)

where $R_5$ is hydrogen or an N-protecting group, and either C is one, D is another and E is the remainder of —$(CH_2)_r$—, —$(CH_2)_s$— and —$(CH_2)_r$—CHA'—$CH_2$— or groups convertible thereto, A' is Z or a group convertible thereto and $L_3$ is a leaving group; or C is one and E is the other of —$(CH_2)_r$— and —$(CH_2)_s$— or groups convertible thereto and D represents —$(CH_2)_r$—CHA'—$CH_2$— where A' and $L_3$ together represent —COO—, and thereafter, optionally or as necessary and in any appropriate order, converting C, D and E to —$(CH_2)_r$—, —$(CH_2)_s$— and —$(CH_2)_r$—CHA'—$CH_2$—, removing any $R_5$ protecting group, converting A' to Z, optionally interconverting Z and/or forming a pharmaceutically acceptable salt; or (c) cyclising a compound of formula (IV):

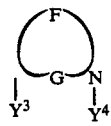

(IV)

where F is one and G is the other of —$(CH_2)_r$— and —$(CH_2)_2$— or groups convertible thereto, and one of $Y^3$ and $Y^4$ is —$(CH_2)_u$—K and the other is —$(CH_2)_v$W or —$(CH_2)_v L_4$ where K and W are electron withdrawing groups, $L_4$ is a leaving group, u is 1 or 2 and v is 0 or 1, with the provisos that when $Y^4$ is —$(CH_2)_v$W, v is 1, and $Y^4$ is not —$(CH_2)_v L_4$, u and v being such that the desired compound of formula (I) is obtained, and thereafter, optionally or as necessary and in any appropriate order, hydrolysing and decarboxylating the cyclisation product and converting the carbonyl group to CHA' where A' is Z or a group convertible thereto, converting K to A' as defined, converting A' to Z, converting F and G to —$(CH_2)_r$— and —$(CH_2)_s$— as appropriate, interconverting Z and/or forming a pharmaceutically acceptable salt.

It will be appreciated that the product of process variant (a) is a compound of formula (I) in which variable Y is hydrogen and that the product of process variant (b) or (c) is a compound of formula (I) in which variable X is hydrogen.

In process variant (a), examples of the leaving groups $L_1$ and $L_2$ include halo such as chloro or bromo, tosyloxy and mesyloxy.

Examples of $R_5$ when an N-protecting group include benzyl and substituted benzyl.

Examples of A and A' include hydroxy, alkoxycarbonyl, benzyloxycarbonyl and cyano.

The cyclisation reaction is a nucleophilic substitution which may be carried out under conventional conditions appropriate to the groups A and B. Thus, when B is $(CH_2)_j$Br and A is $C_{1-4}$ alkoxycarbonyl, the cyclisation is carried out in an inert solvent such as toluene or ether at elevated temperature. When B is $(CH_2)_j$OTos or $(CH_2)_j$O-Mes, it is preferably obtained by treatment of a $(CH_2)_j$OH group with a suitable reagent such as tosylchloride or mesyl chloride, in a base such as pyridine, whereupon the cyclisation may proceed at ambient temperature, or at elevated temperature in an inert solvent such as toluene. When A and $L_1$ together represent —COO—, the cyclisation may be carried out in a lower alkanol such as ethanol in the presence of acid such as hydrogen bromide. In the resulting compound of formula (IIa), A' will be an alkoxycarbonyl group corresponding to the lower alkanol used for the cyclisation.

Where $R_5$ is an N-protecting group such as benzyl, this may be removed by conventional hydrogenation, preferably catalytically over a suitable catalyst such as Pd/C. Where A' or K is benzyloxycarbonyl, deesterification and deprotection may be effected simultaneously by conventional hydrogenation.

Examples of A when an electron withdrawing group include $C_{1-4}$ alkoxycarbonyl and cyano.

When A is an electron withdrawing group such as $C_{1-4}$ alkoxycarbonyl, B is hydrogen and $R_5$ is —$(CH2)_j L_2$ where $L_2$ is, for example, chloro, the cyclisation may be effected by treatment of the compound of formula (II) with lithium diisopropylamide.

In process variant (b), examples of leaving groups $L_3$ include halo such as chloro, hydroxy and tosyloxy. In the group —$(CH_2)_r$—CHA'—$CH_2$—, examples of A' include hydroxy, cyano and formyl. In process variant (c), examples of $L_4$ include those given for $L_3$. Examples of electron withdrawing groups K and W include $C_{1-4}$ alkoxycarbonyl and cyano.

In process variant (b), where $L_3$ is hydroxy and D is —$(CH_2)_r$—CHOH—$CH_2$—, the cyclisation of compounds of formula (III) may be carried out by pyrolysis, by the method of D. O. Spry and H. S. Aaron, J. Org. Chem., 1969, 34, 3674, to yield a compound where A' is hydroxy.

Where E is —$(CH_2)_r$—CO—$CH_2$—, the cyclisation may be carried out under basic conditions where $R_5$ is benzyl (F. I. Carrol, A. M. Ferguson, and J. B. Lewis, J. Org. Chem. 31, 2957, 1966).

Where $L_3$ and A' together represent —COO—, the cyclisation is a rearrangement reaction which can be carried out under acid conditions in a polar solvent, such as hydrogen bromide in ethanol, at ambient temperature, to yield a compound where A' is a carboxy ester group. It is preferred to protect the nitrogen atom with an $R_5$ N-protecting group such as benzyl, which may be subsequently removed by hydrogenation over a suitable catalyst such as Pd/C.

In process variant (c), where $Y^3$ and $Y^4$ both contain carboxy ester groups the cyclisation of compounds of formula (IV) is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

In process variant (c) where $Y^3$ and $Y^4$ both contain cyano groups the cyclisation of compounds of formula (IV) is a Thorpe reaction which is catalysed by a base such as potassium t-butoxide at elevated temperature in a solvent such as toluene.

The resulting β-keto nitrile is hydrolysed and decarboxylated under conventional conditions such as heating at reflux in dilute hydrochloric acid.

Where $Y^3$ is —$(CH_2)_v L_4$, the cyclisation may be carried out as described in EP-0094742 under basic conditions such as sodium hydride and potassium t-butoxide, in an inert polar solvent such as dimethylformamide.

Conversions of the carbonyl group from process variants (b) and (c) and of groups A' and K, and interconversions of Z, may be carried out conventionally, see for example standard text books on heterocyclic chemistry such as 'Comprehensive Heterocyclic Chemistry', A. R. Katritzky and C. W. Rees, Pergamon, 1984.

The carbonyl group may be reacted with tosylmethyl isocyanide to yield a compound where A' is cyano.

The carbonyl group may be reduced to an A' hydroxy group with a suitable reducing agent such as sodium borohydride in ethanol at ambient temperature, or sodium in ethanol at elevated temperature, such as the boiling point of the solvent, under an inert atmosphere such as nitrogen, depending on the stereochemistry required.

An A' hydroxy group may be converted to cyano by first converting it to a good leaving group such as mesyloxy or tosyloxy and then displacing it with cyanide ion.

An A' hydroxy group may be oxidised to a carbonyl group by treatment with chromic acid or using dimethyl sulphoxide and dicyclohexylcarbodiimide.

The A' or K group is first converted, as necessary, to a suitable starting group Z' for the chosen conversion reaction to give the required group Z.

A Z' carboxy group may be obtained by conventional de-esterification of an A' alkoxycarbonyl group.

A Z' chlorocarbonyl group may be obtained by treatment of a Z' carboxy group with thionyl chloride at elevated temperature.

A Z' N-methoxy-N-methylcarboxamido group may be obtained by treatment of a Z' chlorocarbonyl group with N,O-dimethyl hydroxylamine hydrochloride in the presence of pyridine in a suitable solvent such as dichloromethane.

A Z' aminocarbonyl group may be obtained by treatment of a Z' chlorocarbonyl group with ammonia.

A Z' cyano group may be obtained by treatment of a Z' aminocarbonyl group with a dehydrating agent such as phosphorus pentoxide in toluene, or pyridine and trifluoroacetic anhydride.

A Z' $CH_3CO-$ group may be obtained by treatment of a LiOOC group with methyl lithium, the LiOOC group being obtained by hydrolysis of an A' alkoxycarbonyl group with lithium' hydroxide in water. Alternatively and preferably, a Z' $CH_3CO-$ group may be obtained by reaction of a Z' N-methoxy-N-methylcarboxamido group with methyl lithium. A Z' $CH_3CO-$ group may also be obtained by treatment of a cyano group with methyl lithium.

A Z' bromomethylcarbonyl group may be obtained by treatment of a Z' $COCH_3$ group either with bromine in a suitable solvent such as methanol, the nitrogen of the azabicycle being protected as the hydrochloride or hydrobromide salt, or with lithium diisopropylamide and trimethylsilyl chloride at low temperature followed by N-bromosuccinimide in tetrahydrofuran at low temperature. Alternatively, a Z' —COCl group may be converted to a —$COCH_2Br$ group by treatment with diazomethane in ether at low temperature followed by hydrogen bromide in acetic acid at ambient temperature.

A Z' —COCHO group may be obtained by treatment of a Z' bromomethylcarbonyl group with dimethylsulphoxide followed by heating at elevated temperature.

Alternatively, and the preferred route where compounds of formula (I) in which X is hydrogen are to be prepared, the required keto aldehyde intermediate may be generated in protected form via Pummerer rearrangement of a precursor β-ketosulphoxide —$COCH_2SOR'$(where R'=alkyl or aryl). The ketosulphoxide can be reacted with a carboxylic acid anhydride, preferably trifluroacetic anhydride. The resulting keto aldehyde protected as the α-trifluoroacetoxy sulphide can be converted to the required triazine directly. The Pummerer rearrangement of sulphoxides using trifluoroacetic anhydride has been described by H. Sugihara, R. Tanikaga and A. Kaji, Synthesis, 881 (1978). Alternatively the Pummerer rearrangement can be carried out using an acid e.g. hydrochloric acid or trifluoroacetic acid. The resulting β-keto hemithioacetal can be deprotected to give the keto aldehyde intermediate using reported procedures e.g. mercury (II) chloride or copper (II) chloride.

The β-ketosulphoxide intermediate may be prepared by treatment of a Z' N-methoxy-N-methylcarboxamido group with the anion derived from either methylphenylsulphoxide or dimethylsulphoxide. The anion can be generated with a base such as lithium diisopropylamine or n-butyllithium.

Alternatively the β-ketosulphoxide may be prepared by reacting the approxiate sulphoxide with a carboxylic acid ester (A' =alkoxycarbonyl) in the presence of a base such as potassium t-butoxide.

The conversion of a Z'—COCHO group or protected form thereof to the required 5-substituted-1,2,4-triazinyl group Z may be effected by treatment with an appropriately substituted amidrazone $RC(NH_2)=NNH_2$ according to the procedure described by H. Neunhoeffer et al., Tetrahedron Lett., 1969 37 3147. The amidrazones are either known compounds or can be prepared via established routes. Formamidrazone can be generated in situ and used without isolation as described by H. Neunhoeffer and F. Weischedel Liebigs Ann. Chem. 1971 749 16. The reaction may be carried out in a suitable hydroxylic solvent such as methanol or water. When an acid salt of the amidrazone, such as the hydrochloride salt, is used, it is necessary to add a base such as pyridine. Where the keto aldehyde is protected as the α-trifluoroacetoxy sulphide the required triazine may be prepared directly by treating the α-trifluoroacetoxy sulphide with the appropriate amidrazone in the presence of a base such as sodium bicarbonate. Where R is amino, the reagent is an aminoguanidine derivative such as the bicarbonate and the reaction is preferably carried out in aqueous medium at pH 4-7. Preparation of compounds where $R=S-R_1$ may be achieved by reacting the keto aldehyde or protected keto aldehyde with an appropriate S—$R_1$isothiosemicarbazide derivative such as S-methyl isothiosemicarbazide hydrogen iodide. Preparation of compounds where $R=O-R_1$ may preferably be achieved by reacting a compound where $R=S-R_1$ with an appropriate alkoxide such as sodium methoxide in methanol at elevated temperature. Alternatively, preparation of compounds where $R=O-R_1$ can be achieved by first hydrolysing a 3-amino triazine to give the corresponding 3-keto triazine. The hydrolysis is carried out under alkaline conditions for example with potassium hydroxide. The 3-keto triazine can be alkylated. For example methylation can then be achieved using agents such as diazomethane. Alkylation usually gives rise to a mixture of products from which the desired product of O-alkylation can be separated. Compounds where R=amino or alkylamino may be prepared by treating a compound where $R=S-R_1$ with ammonia, or the appropriate alkyl amine in a solvent such as ethanol.

Where applicable, an endo isomer may be obtained by epimerisation of a corresponding exo isomer or vice versa, the epimerisation reaction being effected by standard procedures at any convenient stage in the process but preferably before the introduction of the group Y (J. Saunders et al., J. Chem. Soc. Chem. Comm. 1988 p 1618).

In a further aspect the invention provides a process for the preparation of a compound of formula (I), or a pharmaceutically acceptable salt thereof, which process comprises reacting a compound of formula (IVa):

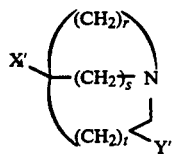
(IVa)

in which r, s and t are as defined in formula (I), one of X' and Y' represents hydrogen and the other represents Z' wherein Z' is a group convertible to Z as defined in formula (I), to convert Z' to Z and thereafter optionally forming a pharmaceutically acceptable salt.

Intermediates of formula (IVb) and salts thereof:

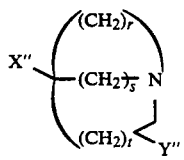
(IVb)

in which r, s and t are defined in formula (I), one of X" and Y" represents hydrogen and the other represents Z" where Z" is —COCHO or a protected form thereof are novel and form part of the invention.

Compounds of formula (II) may be prepared conventionally for example as described in EP-0-287 356.

Where A is $C_{1-4}$ alkoxycarbonyl, B is $(CH_2)_jL_1$ and $R_5$ is hydrogen or an N-protecting group, the compound of formula (II) may be prepared by treating a compound of formula (V):

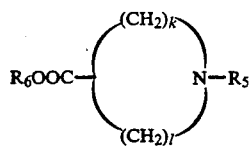
(V)

where $R_6$ is $C_{1-4}$ alkyl and the remaining variables are as previously defined, with lithium diisopropylamide, prepared in situ from diisopropylamine and n-butyllithium followed by reaction with a compound $L_5(CH_2)_jL_1$ where $L_5$ is a leaving group, in an inert solvent such as ether at depressed to elevated temperature. Both $L_1$ and $L_5$ are suitably bromo.

Where A and $L_1$ together represent —COO— and j is 2, the compound of formula (II) may be prepared by reacting the compound of formula (V), treated with lithium diisopropylamide as before, with ethylene oxide in an inert solvent such as ether at depressed to elevated temperature.

Alternatively, the compound of formula (II) where A and $L_1$ together represent —COO, k is 2 and 1 is 1 may be prepared by a 1,3-dipolar cycloaddition reaction which involves reacting a compound of formula (VI):

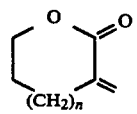
(VI)

where n is 0 or 1, with a compound of formula (VII):

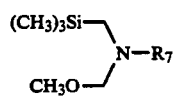
(VII)

in which $R_7$ is an N-protecting group, in the presence of a catalytic amount of trifluoroacetic acid.

Where A is an electron withdrawing group such as $C_{1-4}$ alkoxycarbonyl, B is hydrogen and $R_5$ is $(CH_2)_jL_2$, the compound of formula (II) may be prepared by reacting the compound of formula (V) where $R_5$ is hydrogen with a compound $L_5(CH_2)_jL_2$ where $L_5$ is as previously defined, in a solvent such as acetone in the presence of a base such as potassium carbonate. The leaving group $L_5$ is preferably bromo and $L_2$ is preferably chloro.

Compounds of formulae (V) are known compounds or may be prepared by analogous methods to those for preparing known compounds. The compound of formula (V) where k is 2, 1 is 1 and $R_5$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Alternatively, and preferably, a dipolar cycloaddition of a $C_{1-4}$ alkylacrylate with a compound of formula (VII) in the presence of a catalytic amount of trifluoroacetic acid yields a compound of formula (V) directly.

Intermediates of formulae (III) and (IV) are known compounds (e.g. as described in EP-A-0094742 or EP-A-0261763) or may be prepared analogously.

Intermediates of formula (III) where A' and $L_3$ together represent —COO— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

Compound of formula (III) where A' and $L_3$ together represent —COO—, t=0, C is —$CH_2$— and E is —$(CH_2)_2$— or —$(CH_2)_3$ may be prepared by a 1,3-dipolar cyclo addition reaction of a compound of formula (VII) with 5, 6-dihydro-2H-pyran-2-one or 6,7-dihydro-5H-oxepin-2-one in the presence of a catalytic amount of trifluoroacetic acid.

The use of an optical isomer of the compound of formula (III) or (VII) by providing a chiral centre in the N-protecting group $R_5$ or $R_7$ respectively allows the isolation of a single enantiomer of the product of process variant (b) (ref. EP-0398616). Other routes for preparing single enantiomers are described in EP-0398617 and EP-0392803.

Intermediates of formula (III) where $L_3$ is a leaving group are described in, for example, Spry et al., J. Org. Chem., 1969, 34, 3674 and Hasse et al., Chem. Ber., 1960, 93, 1686.

Intermediates of formula (IV) may be prepared from intermediates of formula (V) as described in, for example, Martell et al., J. Pharm. Sci., 1963, 52 (4), 331, Sternbach et al., J.A.C.S., 1952, 74, 2215, Thill et al., J. Org. Chem., 1968, 33, 4376 and EP-0 094 742.

Compounds of formulae (VI) and (VII) may be prepared conventionally. Thus, a compound of formula (VI) may be obtained by the reaction of $\gamma$-butyrolactone with ethyl formate in the presence of base such as sodium hydride followed by reaction of the resulting formyl derivative (as the enol salt) with formaldehyde. A compound of formula (VII) may be obtained by the reaction of the primary amine $R_7NH_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate. or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel or hydrogenated edible fats; emulsifying agents, for example lecithin, sorbitan monooleate or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10–60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention.

Description 1

($\pm$) 1( 1-Azabicyclo [2.2.2 ]oct-3-yl)-2-(phenylsulphinyl) ethanone (D1)

To a stirred solution of n-butyllithium (2.7 ml of a 1.6M solution in hexanes, 4.3 mmol) in dry tetrahydrofuran (5 ml) cooled to $-78°$ C. under nitrogen was added dropwise a solution of diisopropylamine (0.44 g, 4.3 mmol) in dry tetrahydrofuran (5 ml). The mixture was allowed to warm to $-20°$ C., and was maintained at this temperature for 15 min. After cooling to −78° C. a solution of methyl phenyl sulphoxide (0.55 g, 3.9 mmol) in dry tetrahydrofuran (2 ml) was added dropwise while maintaining the temperature below −65° C. The reaction was stirred for a further 5 rain and then a solution of (±) 1-azabicyclo[2.2.2] oct-3-yl-N-methyl-N-methoxycarboxamide (EP 322182, Description 22) (0.65 g, 3.3 mmol) in dry tetrahydrofuran (5 ml) was added rapidly while ensuring that the temperature did not rise above −60° C. After stirring at −78° C. for 1 h, the reaction was allowed to warm to −30° C., and maintained at this temperature for 30 min. The reaction was then poured into vigorously stirred orthophosphoric acid (20ml of a 5% $H_3PO_4$ solution) cooled below 0° C. The aqueous layer was separated, washed with ether (3×20 ml) and then saturated with potassium carbonate. After extraction with chloroform (3×25 ml) the combined organic extracts were dried over sodium sulphate and concentrated in vacuo to give the title compound (D1) as an oil (1.0 g) consisting of a 1:1 mixture of diastereomeric keto sulphoxides. $^1$H NMR (CDCl$_3$) δ:

1.20–1.70 (8H, m) , 2.01 and 2.22 (each 1H, m) , 2.56–3.00 (12H, m) , 3.20 and 3.35 (each 1H, m) , 3.73 and 4.05 (each 1H, d, J=13.5 Hz), 3.88 (2H, ABq, J=17 Hz), 7.50–7.76 (10H, m).

Description 2

(±) 1- (1-Azabicyclo[2.2.1 ]hept-3-yl) -2- (phenylsulphinyl) ethanone (D2)

(±) endo 1-Azabicyclo[2.2.1 ]hept-3-yl-N-methyl-N-methoxycarboxamide (EP 402056, Description 36) was reacted with methyl phenyl sulphoxide using the procedure given in Description 1 to afford the title compound (D2) as a yellow solid (98%) which consisted of a mixture of 4 diastereomeric keto sulphoxides.

$^1$H NMR (CDCl$_3$) δ:
0.88–1.00, 1.08–1.27 and 1.28–1.70 (together 2H, each m) , 2.15–2.28 and 2.32–3.15 (together 8H, each m) , 3.63–4.10 (2H, m) , 7.48–7.78 (5H, m).

Description 3

(3S, 4R) -1-Azabicyclo[2.2.1]hept-3-yl-N-methyl-N-methoxycarboxamide (D3)

A stirred solution of ethyl (3S, 4R)-1-azabicylo[2.2.1-]hept-3-yl carboxylate (EP 0398616, Example 16) (10.5 g, 0.062 mol) in 8M hydrochloric acid (150ml) was heated under reflux for 2.5 h, then concentrated in vacuo. The residue was twice treated with toluene (100 ml) and concentrated to azeotrope out the remaining traces of water. The white solid obtained was treated with thionyl chloride (100 ml) and the mixture heated under reflux for 25 min to give a yellow solution. This was concentrated in vacuo and the residue twice treated with toluene (100 ml) and concentrated to give the acid chloride hydrochloride salt as a beige solid. This product was dissolved in absolute chloroform (200 ml) and the solution added over 20 min to a stirred solution of N, O-dimethylhydroxylamine hydrochloride (7.48 g, 0. 077 mol) and pyridine (24 ml, 0.29 mol) in absolute chloroform (200 ml) at —20° C. under nitrogen. The reaction mixture was allowed to warm to room temperature over 1.5 h, then treated with saturated potassium carbonate solution and the chloroform layer separated. The aqueous was extracted twice with chloroform (100 ml) and the three chloroform solutions combined, dried over sodium sulphate and concentrated in vacuo to leave a yellow oil. This was purified by passage through a short basic alumina column eluting with chloroform to give the title compound (D3) as a colourless oil (10.6 g, 93%) . $^1$H, NMR (CDCl$_3$) δ:

1.35–1.47 (2H, m) , 2.44–2.52 (1H, m) , 2.58–2.74 (2H, m) , 2.76–2.94 (3H, m) , 2.94–3.06 (1H, m) , 3.06–3.18 (1H, m), 3.22 (3H, s) , 3.72 (3H, s) .

Description 4

(3R, 4R) and (3S, 4R) -1- (1-Azabicyclo[2.2.1]hept-3-yl) -2-(phenylsulphinyl) ethanone (D4)

(3S, 4R) -1-(1-Azabicyclo[2.2.1]hept-3-yl)-2-(phenylsulphinyl) ethanone (D4)

(3S, 4R)-1-Azabicyclo[2.2.1]hept-3-yl-N-methyl-N-methoxycarboxamide (D3) was reacted with methyl phenyl sulphoxide using the procedure given in Description 1 to afford a yellow semi-solid (95%) containing a mixture of the title compounds (D4).

$^1$H NMR (CDCl$_3$) δ:
0.87–1.00, 1.07–1.27 and 1.32–1.70 (together 2H, each m) , 2.15–2.30 and 2.35–3.15 (together 8H, each m) , 3.65–4.10 (2H, m) , 7.52–7.75 (5H, m).

EXAMPLE 1

(±) 5-(3-Methyl-1,2,4-triazin-5-yl)-1-azabicyclo[3.2.-1]octane (E1)

A solution of 5- (α-bromoacetyl) -1-azabicyclo[3.2.-1]octane hydrobromide (EP-0287356, Description 27) (0.5 g, 1.6 mmol) in dry dimethylsulphoxide (10 ml) was stirred overnight at 30° C. The reaction was concentrated under high vacuum keeping the water bath temperature at 50°–60° C. The residue was placed in an oil bath at 125° C. for 4 min. A stream of nitrogen was passed through the reaction vessel during this period, and dimethylsulphide was trapped in a solution of sodium hypochlorite. The resulting (±) 2-oxo-2- ( 1-azabicyclo [3.2.1]oct-5-yl) ethanal hydrobromide was immediately treated with a solution of acetamidrazone hydrochloride* (0.18 g, 1.6 mmol) in methanol containing pyridine (0.31 ml, 1.6 mmol). After stirring overnight at room temperature the reaction was concentrated in vacuo. The residue was treated at ice temperature with a saturated solution of potassium carbonate (5 ml) and extracted into chloroform (3×10 ml). After drying over sodium sulphate the combined organic layers were concentrated in vacuo. Flash chromatography on neutral alumina using 2% ethanol in chloroform as eluant afforded the title compound (E1) (60 mg, 18%) which was converted into the oxalate salt.

*H. Neunhoeffer and F. Weischedel, Liebigs Ann. Chem. 749, 16 (1971).

Oxalate salt:
$^1$H NMR (d$_6$-DMSO) δ: 1.70–2.45 (6H, m) , 2.76 (3H, s) , 3.15–3.65 (6H, m) , 9.45 (1H, s).
$^{13}$C. NMR (d$_6$-DMSO) δ:
16.99, 23.45, 31.11, 33.56, 47.65, 49.96, 51.31, 58.63, 146.31, 162.50, 164.69, 165.68

EXAMPLE 2

(±) 5-(3-Amino-1,2,4-triazin-5-yl)-1-azabicyclo[3.2.1]octane (E2)

(±) 5-(α-Bromoacetyl) -1-azabicyclo[3.2.1]octane hydrobromide (1.0 g, 3.2 mmol) was converted into (±) 2-oxo-2-(1-azabicyclo[3.2.1]oct-5-yl) ethanal hydrobromide as described in Example 1. The crude aldehyde was immediately treated with a suspension of aminoguanidine bicarbonate (0.46 g, 3.38 mmol) in water (15 ml) and the solution was acidified to pH4 with 5M HCl. After stirring overnight at room temperature the reaction mixture was saturated with potassium carbonate then extracted into chloroform. The combined organic extracts were dried over sodium sulphate, concentrated in vacuo and the residue chromatographed on neutral alumina in a gradient of 0-8% methanol in chloroform. This afforded the title compound (E2) as a solid (95 mg, 15%) which was converted into the oxalate salt m.p. 184° C. (dec) (from methanol-ether)..

Oxalate salt: 1H Nmr (d$_6$-DMSO) δ: 1.92-2.56 (6H, m), 3.34-3.80 (6H, m), 7.45 (2H, m), 8.88 (1H, s) 13C Nmr (d$_6$-DMSO) δ:

16.96, 31.06, 33.50, 47.37, 49.79, 51.25, 58.53, 138.35, 162.44, 162.91.

Analysis: $C_{12}H_{17}N_5O_4$ requires: C, 48.81; H, 5.80; N, 23.72.

found: C, 48.44; H, 5.74; N, 23.57.

EXAMPLE 3

4-(3-Methyl-1,2,4-triazin-5-yl)-1-azabicyclo[2.2.1]heptane (E3)

A solution of 4-(α-bromoacetyl)-1-azabicyclo[2.2.1]heptane hydrobromide (EP-0366304, Description 19) (3.0 g, 10.0mmol) in dry dimethylsulphoxide (50 ml) was stirred overnight at room temperature. The reaction was concentrated in vacuo ensuring that the water bath temperature did not exceed 60° C. Co-distillation with successive portions of toluene was used to remove residual dimethylsulphoxide. The residue was placed in an oil bath at 120° C. for 5 min. A stream of nitrogen was passed through the reaction vessel during this period, and the dimethylsulphide which was generated was trapped in a solution of sodium hypochlorite. The resulting crude 2-oxo-2-(1-azabicyclo[2.2.1]hept-4-yl) ethanal hydrobromide was immediately treated with a solution of acetamidrazone hydrochloride (1.1 g, 10.0 mmol) in dry methanol (30 ml) containing pyridine (0.8 ml, 10.0 mmol). The mixture was stirred overnight at room temperature and then heated under reflux for 1 h. The reaction was concentrated in vacuo, and the residue was treated at ice temperature with a saturated solution of potassium carbonate (25 ml). After extraction with chloroform (3×25 ml) the combined organic layers were dried over sodium sulphate and concentrated in vacuo. The resulting crude product was purified on a neutral alumina column using 1% ethanol in chloroform as eluant to give the title compound (E3) as an oil (0.63 g, 33%) which was converted into the hydrochloride salt m.p. 222° C. (dec) (from methanol-ether) . Hydrochloride salt:

$^1$H NMR (d$_6$-DMSO) δ: 2.10-2.40 (4H, m), 2.75 (3H, s), 3.40-3.65 (6H, m), 9.52 (1H, s).

$^{13}$H NMR (d$_6$-DMSO) δ:

23.41, 31.87, 51.40, 52.25, 59.59, 146.66, 158.97, 165.86.

EXAMPLE 4

4-(3-Amino-1,2,4-triazin-5-yl)-1-azabicyclo[2.2.1]heptane (E4).

4-(α-bromoacetyl) -1 -azabicyclo[2.2.1 ]heptane hydrobromide (EP-0366304, Description 19) (0.5 g, 1.67 mmol) was converted into 2-oxo-2- (1-azabicyclo[2.2.1]hept-4-yl)ethanal hydrobromide as described in Example 3. The crude aldehyde was immediately treated with a suspension of aminoguanidine bicarbonate (0.25 g, 1.84 mmol) in water (10 ml) and the solution was acidified to pH6 with 5M hydrochloric acid. After stirring overnight at room temperature the reaction mixture was saturated with potassium carbonate then extracted into chloroform (4×20 ml). The combined organic extracts were dried over sodium sulphate and concentrated in vacuo. The residue was crystallised from isopropanolpentane to afford the title compound (E4) as a brown solid (0.14 g, 43%) . This was converted into the oxalate salt m.p. 178° C. (dec) (from methanol-ether).

Oxalate salt:

$^1$H Nmr (d$_6$-DMSO) δ: 2.10-2.38 (4H, m), 3.37-3.65 (6H, m), 7.37 (2H, s), 8.83 (1H, s) 13C. Nmr (d$_6$-DMSO) δ:

32.07, 51.41, 52.41, 59.69, 138.71, 159.55, 162.62.

Analysis: $C_{11}H_{15}N_5O_4$ requires: C, 46.97; H, 5.38; N, 24.90 found: C, 46.61; H, 5.43; N, 24.58

EXAMPLE 5

4-(3-Methoxy-1,2,4-triazin-5-yl)-1-azabicyclo[2.2.1]heptane (E5)

A solution of 4-(3-Amino-1,2,4-triazin-5-yl)-1-azabicyclo[2.2.1]heptane (E4) (0.5 g, 2.6 mmol) in water (5 ml) was treated with potassium hydroxide (0.29 g, 5.2 mmol) then heated at reflux for 7 h. A further addition of potassium hydroxide (0.29 g) was made during this period. The reaction was concentrated in vacuo, dissolved in dry methanol (5 ml) then treated dropwise with methanolic hydrogen chloride to pH4. The solution was concentrated in vacuo and co-distilled with successive portions of toluene to remove the last traces of solvent. The residue was dissolved in dry dimethylsulphoxide (20 ml) and treated with diazomethane (21 ml of a 0.635M solution in ether, 13.1 mmol) under nitrogen. After stirring at room temperature for 30 min the reaction was acidified with acetic acid and concentrated in vacuo. The residue was treated with saturated aqueous potassium carbonate (5 ml) and extracted into chloroform (3×10 ml). The combined organic extracts were dried over sodium sulphate, and concentrated in vacuo. The residue was chromatographed on silica in a gradient of 0-5% methanol in chloroform. Pooling of pure fractions containing the faster running component of the mixture afforded the title compound (E5) (23 mg) which was converted into the oxalate salt.

Oxalate salt:

$^1$H NMR (d$_6$-DMSO) δ: 2.08-2.39 (4H, m), 3.34-3.66 (6H, m), 4.11 (3H, s), 9.35 (1H, s).

$^{13}$C. NMR (d$_6$-DMSO) δ:

31.96, 51.46, 52.45, 55.46, 59.77, 144.06, 162.10, 163.48

Observed mass=206.1167. Calculated mass for $C_{10}H_{14}N_4O$=206.1172.

EXAMPLE 6

(±)3-(3-Amino-1,2,4-triazin-5-yl)-1-azabicyclo[2.2.2]octane (E6)

(±) 3-(α-Bromoacetyl)-1-azabicyclo [2.2.2 ]octane hydrobromide (EP-0366304, Description 7) (1.0 g, 3.2 mmol) was converted into (±) 2-oxo-2-(1-azabicyclo[2.2.2]octan-3-yl)ethanal hydrobromide using the method described in Example 3. The crude aldehyde was immediately treated with a suspension of aminoguanidine bicarbonate (0.48 g, 3.5 mmol) in water (10 ml), and the solution was acidified to pH4 with 5M hydrochloric acid. The reaction mixture was stirred overnight at room temperature then heated under reflux for 1 h. It was then saturated with potassium carbonate and extracted into chloroform (4×10 ml). The combined organic extracts were dried over sodium sulphate, concentrated in vacuo and the residue chromatographed on neutral alumina in a gradient of 0-8% methanol in chloroform. This afforded the title compound (E6) as a colourless solid (42 mg, 6%) which was converted into the oxalate salt m.p. 175° C. (dec) (from methanol - ether).

Oxalate salt: $^1$H Nmr (d$_6$-DMSO) δ: 1.55-1.83 (2H, m), 1.96-2.20 (2H, m), 2.38-2.47 (1H, m), 3.20-3.61 (6H, m), 3.78-3.94 (1H, m), 7.35 (2H, m), 8.76 (1H, s)
$^{13}$C. Nmr (d$_6$-DMSO) δ:
18.06, 23.30, 24.90, 37.09, 45.21, 45.40, 46.46, 140.45, 161.05, 162.42

Analysis: C$_{10}$H$_{15}$N$_5$ 1.25 C$_2$H$_2$O$_4$
Requires: C, 47.24; H, 5.55; N, 22.04
Found: C, 47.21; H, 5.64; N, 22.23

Example 7

(±) 3-(3-Methyl-1,2,4-triazin-5-yl)-1-azabicyclo[2.2.2]octane (E7)

Method A (±) 3-(α-Bromoacetyl)-1-azabicyclo[2.2.2]octane hydrobromide (EP-0366304, Description 7) (0.5 g, 1.6 mmol) was converted into (±) 2-oxo-2-(1-azabicyclo[2.2.2]octan-3-yl)ethanal hydrobromide using the method described in Example 3. The crude aldehyde was immediately treated with a solution of acetamidrazone hydrochloride (0.18 g, 1.6 mmol) in dry methanol (6 ml) containing pyridine (0.13 ml, 1.6 mmol). The mixture was stirred at room temperature for 48 h, and then concentrated in vacuo. The residue was treated with a saturated aqueous solution of potassium carbonate (10 ml) and extracted into chloroform (4×10 ml). The combined organic layers were dried over sodium sulphate and concentrated in vacuo. The resulting crude oil was purified on neutral alumina using a graded eluant of 1-2% ethanol in chloroform to give the title compound (E7) as a yellow oil (16 mg, 5%).

$^1$H NMR (CDCl$_3$) δ: 1.35 (1H, m), 1.55 (1H, m), 1.80 (2H, m), 2.10 (1H, m), 2.75-3.10 (5H, m and 3H, s), 3.20 (1H, m), 3.55 (1H, dd, J=14 Hz, 5 Hz), 9.0 (1H, s).

Method B

A solution of (±) 1-(1-azabicyclo[2.2.2]oct-3-yl)-2-(phenylsulphinyl)ethanone (D1) (1.0 g) in dry dichloromethane (15 ml) was cooled in ice under nitrogen and treated dropwise with trifluoroacetic anhydride (0.93 ml, 6.6 mmol) over a period of 5-10 min. After a further 45 min at ice temperature the reaction was concentrated in vacuo. Further drying under high vacuum produced a foam which was immediately treated with an aqueous solution (25 ml) containing acetamidrazone hydrochloride (0.72 g, 6.6 mmol) and sodium bicarbonate (1.1 g, 13.2 mmol). The mixture was stirred vigorously at ice temperature for 30 min and then at room temperature for a further 6 h. The solution was saturated with potassium carbonate and extracted with chloroform (3×25 ml). The combined organic extracts were dried over sodium sulphate and concentrated in vacuo to give a gum. Purification by flash chromatography on neutral alumina using a graded eluant of 1-3% methanol in chloroform afforded the title compound (E7) as a gummy solid (0.15 g) which was further purified by recrystallisation of the oxalate salt m.p. 153-154° C. (from acetone-methanol).

Oxalate salt: $^1$NMR (d$_6$-DMSO) δ: 1.42-1.75 (2H, m), 1.87-2.14 (2H, m), 2.40 (1H, m), 2.78 (3H, s), 3.10-3.35 (4H, m), 3.50 (1H, m), 3.60 (1H, m) 3.80 (1H, m) 9.40 (1H, s). $^{13}$C. NMR (d$_6$-DMSO) δ:
18.23, 23.75, 23.86, 25.46, 37.81, 45.55, 45.76, 46.96, 148.67, 161.29, 165.08, 165.80.

EXAMPLE 8

(±) exo and endo 3-(3-Methyl-1,2,4-triazin-5-yl)-1-azabicyclo[2.2.1]heptane (E8a) and (E8b)

Method A (±) exo and endo 3-(α-bromoacetyl)-1-azabicyclo[2.2.1]heptane hydrobromide (7:1 ratio of exo:endo isomers) (EP-0366304, Description 23) (1.3 g, 4.35mmol) was converted into (±) exo and endo 2-oxo-2-(1-azabicyclo[2.2.1]hept-3-yl)ethanal hydrobromide using the method described in Example 3. The crude aldehyde was immediately treated with a solution of acetamidrazone hydrochloride (0.52 g, 4.75 mmol) in dry methanol (15 ml) containing pyridine (0.6 ml). After stirring at room temperature for 4 days, the solvent was removed in vacuo. The residue was treated with saturated aqueous potassium carbonate (15 ml) and extracted into chloroform (3×20 ml). The combined organic extracts were dried over sodium sulphate and concentrated in vacuo. The residue was purified by repeated flash chromatography on silica in a gradient of 0-10% methanol in chloroform. This afforded a 7:1 mixture of the title compounds (E8a) and (E8b) as a gum (66mg, 8%) which was converted into the oxalate salt.

Oxalate salt: $^1$H NMR (d$_6$-DMSO) : (Signals corresponding to major exo isomer) δ:
1.90 (1H, m), 2.15 (1H, m), 2.85 (3H, s), 3.12-4.09 (8H, m), 9.48 (1H, s).

Observed mass=190.1218. Calculated mass for C$_{10}$H$_{14}$N$_4$=190.1219.

Method B

A solution of (±) 1-(1-azabicyclo[2.2.1]hept-3-yl)-2-(phenylsulphinyl)ethanone (D2) (0.779 g, 3.0 mmol) in dry dichloromethane (20 ml) was cooled in ice and treated dropwise with trifluoroacetic anhydride (0.85 ml, 6.0 mmol). After stirring at ice temperature for a further 45 min the reaction was concentrated in vacuo. Following further drying under high vacuum the residue was treated with an aqueous solution (20 ml) containing acetamidrazone hydrochloride (0.66 g, 6.0 mmoles) and sodium bicarbonate (0.76 g, 9.0 mmol). The mixture was stirred overnight and then worked up as described in Example 7 (Method B) to give a mixture of the title compounds (E8a) and (E8b) which was separated by flash chromatography on neutral alumina using a graded eluant of 1-1.5% methanol in chloroform. Pooling of pure fractions containing the major faster running component afforded the exo isomer (E8a) as an oil (0.12 g, 21%) which was converted into the oxalate salt m.p. 135°-136.5° C. (from acetone-methanol).

Oxalate salt:
$^1$H NMR (d$_6$-DMSO) δ:
1.90 (1H, m), 2.15 (1H, m), 2.85 (3H, s), 3.08-3.90 (8H, overlapping m), 9.48 (1H, s).
23.49, 27.44, 41.66, 43.51, 51.52, 54.87, 56.17, 148.25, 160.73, 164.59, 165.60.

EXAMPLE 9

(±) exo and endo 3-(3-Amino-1,2, 4-triazin-5-yl) -1-azabicyclo[2.2.1]heptane (E9a) and (E9b) (±)1-(1-Azabicyclo[2.2.1]hept-3-yl )-2-(phenylsulphinyl) ethanone (D2) (0.5 g, 1.9 mmol) was treated with trifluoroacetic anhydride as in Example 8 (Method B). The crude product was treated with a suspension of aminoguanidine bicarbonate (0.52 g 3.8 mmol) in water (15 ml). After stirring at room temperature overnight the solution was cooled in ice, saturated with potassium carbonate and extracted into chloroform (3×15 ml). The combined organic extracts were dried over sodium sulphate, concentrated in vacuo then chromatographed on neutral alumina in a gradient of 0–4% ethanol in chloroform. This afforded a 3:1 mixture of the title compounds E9a and E9b as a colourless solid (51 mg, 14%) which was converted into the oxalate salt m.p. 162° C. (dec) (from methanol-ether).

Oxalate salt:

$^1$H NMR (d$_6$-DMSO) (signals corresponding to major exo isomer) δ:
1.81–1.99 (1H, m), 2.05–2.21 (1H, m), 3.08–3.89 (8H, m), 7.34 (2H, br, s), 8.75 (1H, s).

$^{13}$C NMR (d$_6$-DMSO) (signals corresponding to major exo isomer) δ:
27.32, 41.58, 43.05, 51.46, 54.63, 56.22, 140.36, 160.83, 162.55, 164.36.

EXAMPLE 10

(±) exo and endo 3-(3-Ethyl-1,2,4-triazin-5-yl) -1-azabicyclo[2.2.1]heptane (E10a) and (E10b)

(±) 1- (1-azabicyclo[2.2.1]hept-3-yl) -2- (phenylsulphinyl) ethanone (D2) (0.79 g, 3.0retool) was treated with trifluoroacetic anhydride as described in Example 8 (Method B). The crude product was treated with an aqueous solution (20 ml) containing propionamidrazone hydrochloride* (0.74 g, 6.0 mmol) and sodium bicarbonate (0.76 g, 9.0 mmol). The mixture was stirred at room temperature for 4 h and then worked up as described in Example 7 (Method B). The crude product, consisting of a 4:1 mixture of exo and endo isomers (E10a) and (E10b), was extracted into ether and then purified by flash chromatography on silica using a graded eluant of 5–15% methanol in chloroform. Pooling of pure fractions containing the major faster running component afforded the exo isomer (E10a) as a pale yellow oil (90 mg, 15%).

*Prepared using the procedure described by W. Oberhummer, Monatsh. Chem., 63,285 (1933).

$^1$H NMR (CDCl$_3$) δ: 1.30–1.45 (3H, t, J = 7Hz and 1H, m) , 1.72 (1H, m) , 2.40 (1H, m) , 2.55–2.72 (2H, m) , 2.80 (1H, m) , 2.88–3.05 (3H, m), 3.11 (2H, q, J=7Hz), 3.25 (1H, m), 8.97 (1H, s).

$^{13}$C NMR (CDCl$_3$) δ:
12.35, 30.61, 30.65, 43.64, 47.16, 53.94, 58.32, 60.38, 147.49, 163.68, 170.30.

Oxalate salt m.p. 73–75° C. (acetone–methanol) (hygroscopic).

EXAMPLE 11

(±) exo and endo 3-(3-Methylthio-1,2,4-triazin-5-yl) -1-azabicyclo[2.2.1]heptane (E11a) and (E11b)

(±) 1-(1-Azabicyclo[2.2.1]hept-3-yl) -2- (phenylsulphinyl) ethanone (D2) (0.79 g, 3.0 mmol) was reacted with trifluoroacetic anhydride as described in Example 8 (Method B). The crude product was treated with an aqueous solution (20 ml) containing S-methylisothiosemicarbazide hydrogen iodide* (0.73 g, 3.0mmol) and sodium bicarbonate (0.5 g, 6.0 mmol). The mixture was stirred at room temperature overnight and then worked up as described in Example 7 (Method B). The crude product consisting of a 4:1 mixture of exo and endo isomers (E11a) and (E11b) was purified by flash chromatography on silica using a graded eluant of 5–10% methanol in chloroform. Pooling of pure fractions containing the major faster running component afforded the exo isomer (E11a) as a pale yellow oil (0.15 g, 22%).

*E. Cattelain, Bull. Soc. Chim. Fr., 11, 256, (1944).

$^1$H NMR (CDCL$_3$) δ: 1.27–1.40 (1H, m), 1.63–1.80 (1H, m), 2.40 (1H, m), 2.55–2.68 (3H, s and 2H, m), 2.80 (1H, m), 2.85–3.02 (3H, m), 3.20 (1H, m), 8.80 (1H, s).

Hydrochloride salt m.p. 211°–212° C. (dec) (methanol-ether).

EXAMPLE 12

(±) exo and endo 3- (3-Methoxy-1,2,4-triazin-5-yl) -1-azabicyclo[2.2.1]heptane (E12a) and E(12b)

(±) exo and endo 3-(3-methylthio-1,2,4-triazin-5-yl) -1-azabicyclo[2.2.1]heptane (E11a) and (E11b) (4:1 mixture of exo and endo isomers) (60 mg, 0.27 mmol) was treated with sodium methoxide, generated from sodium (18 mg, 0.78 mmol) in dry methanol (7 ml). The mixture was heated under reflux for 4 h and then concentrated in vacuo. The residue was treated with a saturated solution of potassium carbonate (5 ml) and extracted into chloroform (3÷10 ml). The combined organic layers were concentrated in vacuo to give a yellow oil (50 mg) consisting of a 4:1 mixture of the title compounds (E12a) and (E12b). Purification by chromatography as described in Example 11 afforded the title exo isomer (E12a) .

$^1$H NMR (CDCl$_3$) δ:
1.30 (1H, m) , 1.70 (1H, m) , 2.40 (1H, m) , 2.50–2.70 (2H, m), 2.80–3.03 (4H, m), 3.15 (1H, m), 4.18 (3H, s), 8.83 (1H, s).

EXAMPLE 13

3R, 4R) and (3S, 4R) 3-(3-Ethyl-1,2,4-triazin-5-yl)-1-azabicyclo[2.2.1]heptane (E13a) and (E13b)

(3R, 4R) and (3S, 4R) 1-(1-Azabicyclo[2.2.1]hept-3-yl)-2-(phenylsulphinyl) ethanone (D4) (2.0 g, 7.6 mmol) was reacted with trifluoroacetic anhydride as described in Example 8 (Method B). The crude product was treated at ice temperature with an aqueous solution (50 ml) containing propionamidrazone hydrochloride (1.12 g, 9.1 mmol) and sodium bicarbonate (1.28 g, 15.2mmol). The mixture was stirred at room temperature overnight and then worked up as described in Example 7 (Method B). The product was purified by chromatography on silica using 3% methanol in chloroform as eluant. The major component (E13a) was isolated as a pale yellow oil.

$^1$H NMR (CDCl$_3$) δ:
1.29–1.47 (1H, m), 1.41 (3H, t, J=7Hz), 1.65–1.82 (1H, m), 2.37–2.45 (1H, m) 2.54–2.74 (2H, m) , 2.77–2.83 (1H, m), 2.89–3.05 (3H, m), 3.12 (2H, q, J=7Hz), 3.18–3.30 (1H, m), 8.98 (1H, s).

EXAMPLE 14

(±) exo and endo 3-(3-Dimethylamino-1,2,4-triazin-5-yl)-1-azabicyclo[2.2.1]heptane (E14a) and (E14b)

(±) exo and endo 3-(3-Methylthio-1,2,4-triazin-5-yl)-1-azabicyclo[2.2.1]heptane (E11a) and (E11b) (60 mg, 0.27 mmol) was treated with dimethylamine (5 ml of a 33% solution in anhydrous ethanol) and the solution was heated under reflux for 8 h. During this period two further 5 ml aliquots of dimethylamine were added. The reaction was concentrated in vacuo to give a yellow oil containing the title compounds (E14a) and (E14b). Purification by chromatography as described in Example 11 afforded the major exo isomer (E14a).

$^1$H NMR (CDCl$_3$) δ:
1.30 (1H, m), 1.68 (1H, m), 2.32-3.00 (7H, m), 3.13-3.30 (1H, m and 6H, s), 8.39 (1H, s).

EXAMPLE 15

(±) exo and endo 3-(3-Cyclopropyl-1,2,4-triazin-5-yl)-1-azabicyclo[2.2.1]heptane (E15a) and (E15b)

The title compounds (E15a) and (E15b) were prepared from cyclopropanecarboxamide hydrazone hydrochloride* using the method described in Example 13. The crude product, consisting of a 4:1 mixture of exo and endo isomers, was purified by chromatography on silica using a graded eluant of 5-15% methanol in chloroform to give the title exo isomer (E15a) as a pale yellow oil.

*Prepared from ethyl cyclopropanecarboximidate [J. B. Cloke, E. C. Knowles and R. J. Anderson, J. Am. Chem. Soc., 58, 254 (1936)] using the method of W. Oberhummer, Monatsh. Chem., 63, 285 (1933).

$^1$H NMR (CDCl$_3$) δ:
1.18 (4H, d, J = 7Hz), 1.33 (1H, m), 1.70 (1H, m), 2.38 (1H, m), 2.47 (1H, t, J=7Hz), 2.50-2.65 (2H, m), 2.75 (1H, m) 2.85-3.00 (3H, m) 3.15 (1H, m) 8.98 (1H, s).

EXAMPLE 16

(±) exo and endo 3-(1,2,4-Triazin-5-yl)-1-azabicyclo[2.2.1]heptane (E16a) and (E16b)

(±) 1-(1-Azabicyclo[2.2.1]hept-3-yl)-2-(phenylsulphinyl) ethanone (D2) (0.5 g, 1.9mmol) was treated with trifluoroacetic anhydride (0.8 g, 3.8 mmol) as described in Example 8 (Method B). The resulting crude product was dissolved in methanol (5 ml) and added to a solution of formamidrazone cooled to −78° C. The formamidrazone was generated from anhydrous hydrazine (0.06 ml, 1.9 mmol) and formamidine hydrochloride (0.15 g, 1.9 mmol) in methanol (4 ml) following the procedure described by Neunhoeffer and Weischedel*. The mixture was allowed to warm to room temperature overnight, and then concentrated in vacuo to give a crude gum containing the exo and endo isomers (E16a) and (E16b) in a ratio of 4:1. Purification as described in Example 11 afforded the major exo isomer (E16a) as an oil (40 mg, 12%).

*H. Neunhoeffer and F. Weischedel, Liebigs Ann. Chem., 749, 16 (1971).

$^1$H NMR (CDCl$_3$) δ:
1.29-1.41 (1H, m), 1.66-1.81 (1H, m), 2.38-2.46 (1H, m, 2.53-3.06 (6H, m), 3.12-3.23 (1H, m), 9.16 (1H, d, J=3Hz), 9.55 (1H, d, J=3Hz).

|   |    | R    | r | s | t |
|---|----|------|---|---|---|
| Y=H | E1 | CH$_3$ | 3 | 1 | 0 |

|   |    | R    | r | s | t |
|---|----|------|---|---|---|
|   | E2 | NH$_2$ | 3 | 1 | 0 |
|   | E3 | CH$_3$ | 2 | 1 | 0 |
|   | E4 | NH$_2$ | 2 | 1 | 0 |
|   | E5 | OCH$_3$ | 2 | 1 | 0 |
| X=H | E6 | NH$_2$ | 2 | 2 | 0 |
|   | E7 | CH$_3$ | 2 | 2 | 0 |
|   | E8a (exo) | CH$_3$ | 2 | 1 | 0 |
|   | E8b (endo) | CH$_3$ | 2 | 1 | 0 |
|   | E9a (exo) | NH$_2$ | 2 | 1 | 0 |
|   | E9b (endo) | NH$_2$ | 2 | 1 | 0 |
|   | E10a(exo) | C$_2$H$_5$ | 2 | 1 | 0 |
|   | E10b(endo) | C$_2$H$_5$ | 2 | 1 | 0 |
|   | E11a(exo) | SCH$_3$ | 2 | 1 | 0 |
|   | E11b(endo) | SCH$_3$ | 2 | 1 | 0 |
|   | E12a(exo) | OCH$_3$ | 2 | 1 | 0 |
|   | E12b(endo) | OCH$_3$ | 2 | 1 | 0 |
|   | E13a(3R,4R) | C$_2$H$_5$ | 2 | 1 | 0 |
|   | E13b(3S,4R) | C$_2$H$_5$ | 2 | 1 | 0 |
|   | E14a(exo) | N(CH$_3$)$_2$ | 2 | 1 | 0 |
|   | E14b(endo) | N(CH$_3$)$_2$ | 2 | 1 | 0 |
|   | E15a(exo) | cC$_3$H$_5$ | 2 | 1 | 0 |
|   | E15b(endo) | cC$_3$H$_5$ | 2 | 1 | 0 |
|   | E16a(exo) | H | 2 | 1 | 0 |
|   | E16b(endo) | H | 2 | 1 | 0 |

Biological Activity

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H-OXO-M) experiments. For 3H-Quinuclidinyl Benzilate (3H-QNB), 1 ml of stored membranes is diluted to 30 ml and 0.1 ml mixed with test compound and 0.27 nM (c. 25,000 cpm) 3H-QNB (Amersham International). For 3H-OXO-M, 1 ml of membranes is diluted to 6 ml and 0.1 ml mixed with test compound and 2 nM (c. 250,000 cpm) 3H-OXO-M (New England Nuclear).

Non-specific binding of 3H—QNB is defined using 1 μM Atropine sulphate (2 μM Atropine) and of 3H-OXO-M using 10 μM Oxotremorine. Non-specific binding values typically are 5% and 25% of total binding, respectively. Incubations are carried out at 37° C. for 30 min and the samples filtered using Whatman GF/B filters. (In the 3H-OXO experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillahr.

This test provides an indication of the muscarinic binding activity of the test compound. The results are obtained as IC$_{50}$ values (i.e. the concentration which inhibits binding of the ligand by 50%) for the displacement of the muscarinic agonist 3H-OXO-M and the muscarinic antagonist 3H-QNB. The ratio IC$_{50}$(3H-QNB)/IC$_{50}$(3H-OXO-M) gives an indication f the agonist character of the compound. Agonists typically exhibit a large ratio; antagonists typically exhibit a ratio near to unity.

The results are shown in Table 1:

TABLE 1

| Example | [³H-OXO-M IC₅₀ (nM) | ³H-QNB IC₅₀ (nM) |
|---|---|---|
| E1 | 33 | 1800 |
| E2 | 5 | 1114 |
| E3* | 70 | 4400 |
| E4 | 4 | 1494 |
| E5 | 1100 | 14000 |
| E6 | 11 | 2366 |
| E7 | 3.3 | 175 |
| E8a | 3.1 | 255 |
| E9a & E9b | 1.1 | 320 |
| E10 | 68 | 240 |

*Tested as the hydrochloride salt. All other compounds were tested as oxalate salts.

We claim:

1. A compound of formula (I) or a pharmaceutically acceptable salt thereof:

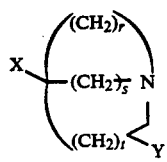  (I)

in which one of X and Y represents hydrogen and the other represents Z, where Z is a group

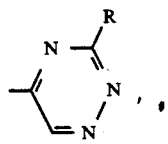

where R is selected from hydrogen, $OR_1$, $SR_1$, $N(R_1)_2$, $NHCOR_1$, $NHCOOCH_3$, $NHCOOC_2H_5$, $NHOR_1$, $NHNH_2$, $C_{2-4}$ alkenyl, $C_{2-4}$ alkynyl, cyclopropyl or $C_{1-2}$ alkyl optionally substituted with $OR_1$, $N(R_1)_2$, $SR_1$, $CO_2R_1$, $CON(R_1)_2$ or one, two or three halogen atoms, in which each $R_1$ is independently hydrogen or $C_{1-2}$ alkyl; r represents an integer of 2 or 3, s represents an integer of 1 or 2 and t represents 0 or 1, with the proviso that when Y is hydrogen s is 1.

2. A compound according to claim 1 wherein (r,s,t) is (2, 2, 0), (3, 1, 0), (2, 1, 0), (2, 1, 1) or (3, 1, 1).

3. A compound according to claim 1 wherein R is hydrogen, $C_{1-2}$ alkyl, cyclopropyl, $OR_1$, $SR_1$ or $N(R_1)_2$.

4. A compound according to claim 3 wherein $R_1$ is hydrogen or methyl.

5. A compound according to claim 1 wherein R is hydrogen, methyl, methoxy, methylthio, cyclopropyl, amino or dimethylamino.

6. (±) 5-(3-Methyl-1,2,4-triazin-5-yl)-1-azabicyclo[3.2.1]octane, (±) 5-(3-amino-1,2,4-triazin-5-yl)-1-azabicyclo[3.2.1]octane, 4-(3-methyl-1,2,4-triazin-5-yl)-1-azabicyclo [2.2.1]heptane, 4-(3-amino-1,2,4-triazin-5-yl)-1-azabicyclo [2.2.1]heptane, 4-(3-methoxy-1,2,4-triazin-5-yl)-1-azabicyclo [2.2.1]heptane, (±) 3-(3-amino-1,2,4-triazin-5-yl)-1-azabicyclo [2.2.2]octane, (±) 3-(3-methyl-1,2,4-triazin-5-yl)-1-azabicyclo[2.2.2]octane, (±) exo 3-(3-methyl-1,2,4-triazin-5-yl)-1-azabicyclo[2.2.1]heptane, (±) endo 3-(3-methyl-1,2,4-triazin-5-yl)-1-azabicyclo[2.2.1]heptane, (±) exo 3-(3-amino-1,2,4-triazin-5-yl)-1-azabicyclo [2.2.1]heptane, (±) endo 3-(3-amino-1,2,4-triazin-5-yl)-1-azabicyclo [2.2.1]heptane, (±) exo 3-(3-ethyl-1,2,4-triazin-5-yl)-1-azabicyclo [2.2.1]heptane, (±) endo 3-(3-ethyl-1,2,4-triazin-5-yl)-1-azabicyclo [2.2.1]heptane, (±) exo 3-(3-methylthio-1,2,4-triazin-5-yl)-1-azabicyclo [2.2.1]heptane, (±) endo 3-(3-methylthio-1,2,4-triazin-5-yl)-1-azabicyclo [2.2.1] heptane, (±) exo 3-(3-methoxy-1,2,4-triazin-5-yl)-1-azabicyclo [2.2.1]heptane, (±) endo 3-(3-methoxy-1,2,4-triazin,5-yl) -1-azabicyclo [2.2.1]heptane, (3R, 4R) 3-(3-ethyl-1,2,4-triazin-5-yl)-1-azabicyclo[2.2.1]heptane, (3S, 4R) 3-(3-ethyl-1,2,4-triazin-5-yl)-1-azabicyclo [2.2.1]heptane, (±) exo 3-(3-dimethylamino-1,2,4-triazin-5-yl)-1-azabicyclo [2.2.1]heptane, (±) endo 3-(3-dimethylamino-1,2,4-triazin-5-yl) -1-azabicyclo [2.2.1]heptane, (±) exo 3-(3-cyclopropyl-1,2,4-triazin-5-yl)-1-azabicyclo[2.2.1]heptane, (±) endo 3-(3-cyclopropyl-1,2,4-triazin-5-yl)-1-azabicyclo[2.2.1]heptane, (±) exo 3-(1,2,4-triazin-5-yl)-1-azabicyclo[2.2.1]heptane or (±) endo 3-(1,2,4-triazin-5-yl)-1-azabicyclo[2.2.1]heptane, or a pharmaceutically acceptable salt of any of the foregoing compounds.

7. A process for the preparation of a compound of formula (I) as defined in claim 1 or a pharmaceutically acceptable salt thereof, which process comprises reacting a compound of formula (IVa):

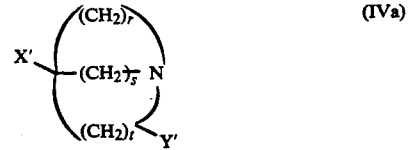  (IVa)

in which r, s and t are as defined in formula (I), one of X' and Y' represents hydrogen and the other represents Z' wherein Z' is COCHO, optionally protected as the α-trifluoroacetoxy sulphide, to convert Z' to Z by treatment with an amidrazone $RC(NH_2)=NNH_2$ and thereafter optionally forming a pharmaceutically acceptable salt.

8. A pharmaceutical composition which comprises a compound according to claim 1 and a pharmaceutically acceptable carrier.

9. A method of treatment and/or prophylaxis of dementia in mammals including humans, which comprises administering to the sufferer an effective amount of a compound according to claim 1.